United States Patent
Weedon et al.

(10) Patent No.: US 10,527,738 B2
(45) Date of Patent: Jan. 7, 2020

(54) RADIATION DETECTOR ARRAY WITH SOLAR CELL

(71) Applicant: Analogic Corporation, Peabody, MA (US)

(72) Inventors: Hans J. Weedon, Salem, MA (US); David Schafer, Rowley, MA (US); Peter Daniel Shippen, Ipswich, MA (US)

(73) Assignee: Analogic Corporation, Peabody, MA (US)

( * ) Notice: Subject to any disclaimer, the term of this patent is extended or adjusted under 35 U.S.C. 154(b) by 293 days.

(21) Appl. No.: 15/527,024

(22) PCT Filed: Nov. 17, 2014

(86) PCT No.: PCT/US2014/065890
§ 371 (c)(1),
(2) Date: May 16, 2017

(87) PCT Pub. No.: WO2016/080945
PCT Pub. Date: May 26, 2016

(65) Prior Publication Data
US 2017/0322321 A1    Nov. 9, 2017

(51) Int. Cl.
*G01N 23/00* (2006.01)
*G01T 1/36* (2006.01)
(Continued)

(52) U.S. Cl.
CPC .......... *G01T 1/2018* (2013.01); *G01N 23/04* (2013.01); *H01L 27/14663* (2013.01)

(58) Field of Classification Search
CPC .......... G01N 23/04; G01N 23/20; G01T 1/20; G01T 1/2018; G01T 1/202; G01T 1/1644;
(Continued)

(56) References Cited

U.S. PATENT DOCUMENTS 4,053,774 A * 10/1977 Berdahl ................ A61B 6/502
378/97
4,070,571 A    1/1978 Gibbons et al.
(Continued)

FOREIGN PATENT DOCUMENTS

| GB | 2144960 A | 3/1985 |
|---|---|---|
| WO | 0042826 A2 | 7/2000 |
| WO | 03096070 A1 | 11/2003 |

OTHER PUBLICATIONS

International Search Report cited in related application No. PCT/US14/65890 dated Aug. 5, 2015 pp. 13.

*Primary Examiner* — Irakli Kiknadze
(74) *Attorney, Agent, or Firm* — TraskBritt

(57) ABSTRACT

A detector array (118) for a radiation system includes first and second detector cells (202, 250). The first detector cell (202) includes a first scintillator (220) that converts a radiation photon (226) impinging the first scintillator (220) into first light energy (230), and a first solar cell (212) that converts the first light energy (230) into first electrical energy. The second detector cell (250) includes a second scintillator (270) that converts a radiation photon (276) impinging the second scintillator (270) into second light energy (280). The first scintillator (220) includes a first detection surface (224) through which the radiation photon (226) impinging the first scintillator (220) enters the first scintillator (220). The second scintillator (270) includes a second detection surface (274) through which the radiation photon (276) impinging the second scintillator (270) enters the second scintillator (270). The second detection surface (274) is substantially parallel to the first detection surface (224) and the second detection surface (274) is not coplanar with the first detection surface (224).

20 Claims, 5 Drawing Sheets

(51) Int. Cl.
*G01T 1/20* (2006.01)
*G01N 23/04* (2018.01)
*H01L 27/146* (2006.01)

(58) Field of Classification Search
CPC ... G01T 1/2985; G01T 1/1642; G01T 1/2002;
G01T 1/201; G01T 1/2023; G01T 1/208;
G01T 1/249; G01T 1/36; G01T 1/29;
G01T 1/2914; G01T 1/2006; G01T 1/24;
H01L 27/14663; H01L 27/308; H01L
51/0007; H01L 51/0035; H01L 51/0037;
H01L 51/0047; H01L 51/0077; H01L
51/4253; H01L 51/442; A61B 6/4258;
A61B 6/032; A61B 6/4021; A61B
5/0536; A61B 6/037; A61B 6/4078; A61B
6/4233; A61B 6/4266; A61B 6/06; A61B
6/4028; A61B 6/4447; A61B 6/4488;
A61B 6/542; A61B 6/585; A61B 6/587;
H01J 2235/068; H01J 35/06; H01J 35/08;
H01J 35/14; G01V 5/0025; G21K 1/025;
G21K 1/046
USPC ...................................... 378/4, 19, 98.9, 82
See application file for complete search history.

(56) References Cited

U.S. PATENT DOCUMENTS

| | | |
|---|---|---|
| 4,492,869 A | 1/1985 | Suzuki et al. |
| 2006/0284602 A1* | 12/2006 | Spahn ................... G03B 42/02 320/166 |
| 2007/0003006 A1 | 1/2007 | Tkaczyk et al. |
| 2011/0278464 A1 | 11/2011 | Clark et al. |
| 2012/0241628 A1 | 9/2012 | Hesser et al. |
| 2015/0317501 A1* | 11/2015 | Safai ................... G06K 7/10366 340/5.8 |

* cited by examiner

RADIATION DETECTOR ARRAY WITH SOLAR CELL

BACKGROUND

The present application relates to an indirect conversion detector array of a radiation system. It finds particular application in medical, security, and/or industrial fields, where radiation imaging systems are used to identify/view interior aspects of an object under examination.

Today, radiation systems such as computed tomography (CT) systems, single-photon emission computed tomography (SPECT) systems, digital projection systems, and/or line-scan systems, for example, are useful to provide information, or images, of interior aspects of an object under examination. The object is exposed to rays of radiation photons (e.g., x-ray photons, gamma ray photons, etc.) and radiation photons traversing the object are detected by a detector array positioned substantially diametrically opposite a radiation source relative to the object. A degree to which the radiation photons are attenuated by the object (e.g., absorbed, scattered, etc.) is measured to determine one or more properties of the object, or rather aspects of the object. For example, highly dense aspects of the object typically attenuate more radiation than less dense aspects, and thus an aspect having a higher density, such as a bone or metal, for example, may be apparent when surrounded by less dense aspects, such as tissue or clothing.

Detector arrays comprise a plurality of detector cells, respectively configured to detect radiation impinging a predefined portion of the detector array. The detector cells are configured to directly or indirectly convert radiation photons into electrical charge. Direct conversion detector cells are configured to convert the radiation photons directly into electrical charge using a photoconductor (e.g., amorphous selenium). Indirect conversion detector cell are configured to convert the radiation photons into light using a scintillator and to convert the light into electrical charge using a photodetector, such as a photodiode. In a detector array comprising indirect conversion detector cells, conventional detector cells include one or more scintillators. The one or more scintillators are arranged such that the radiation photons impinge a detection surface of the detector cells at a perpendicular angle. In this way, a thickness of the one or more scintillators should be sufficient to allow for optical photons to exit the scintillator while not being so thick to mitigate excessive cross-talk between adjacent detector cells.

SUMMARY

Aspects of the present application address the above matters, and others. According to an aspect, a detector array for a radiation system comprises a first detector cell comprising a first scintillator configured to convert a radiation photon impinging the first scintillator into first light energy. The first detector cell comprises a first solar cell configured to convert the first light energy into first electrical energy.

According to another aspect, a detector array for a radiation system comprises a first detector cell comprising a first scintillator configured to convert a radiation photon impinging the first scintillator into first light energy. The first scintillator comprises a first detection surface through which the radiation photon impinging the first scintillator enters the first scintillator. The first scintillator comprises a first solar cell configured to convert the first light energy into first electrical energy. The detector array comprises a second detector cell comprising a second scintillator configured to convert a radiation photon impinging the second scintillator into second light energy. The second scintillator comprises a second detection surface through which the radiation photon impinging the second scintillator enters the second scintillator. The second detection surface is substantially parallel to the first detection surface and the second detection surface is not coplanar with the first detection surface.

According to another aspect, a radiation system comprises a radiation source configured to emit a radiation photon. The radiation system comprises a first detector cell comprising a first scintillator configured to convert the radiation photon impinging the first scintillator into first light energy. The first scintillator comprises a first detection surface through which the radiation photon impinging the first scintillator enters the first scintillator and a first light emission surface through which the first light energy exits the first scintillator. The first detection surface extends along a first detection surface plane that forms a first incidence angle with respect to a first radiation photon axis along which the radiation photon impinging the first scintillator travels. The first incidence angle is greater than 0° and less than 90°.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
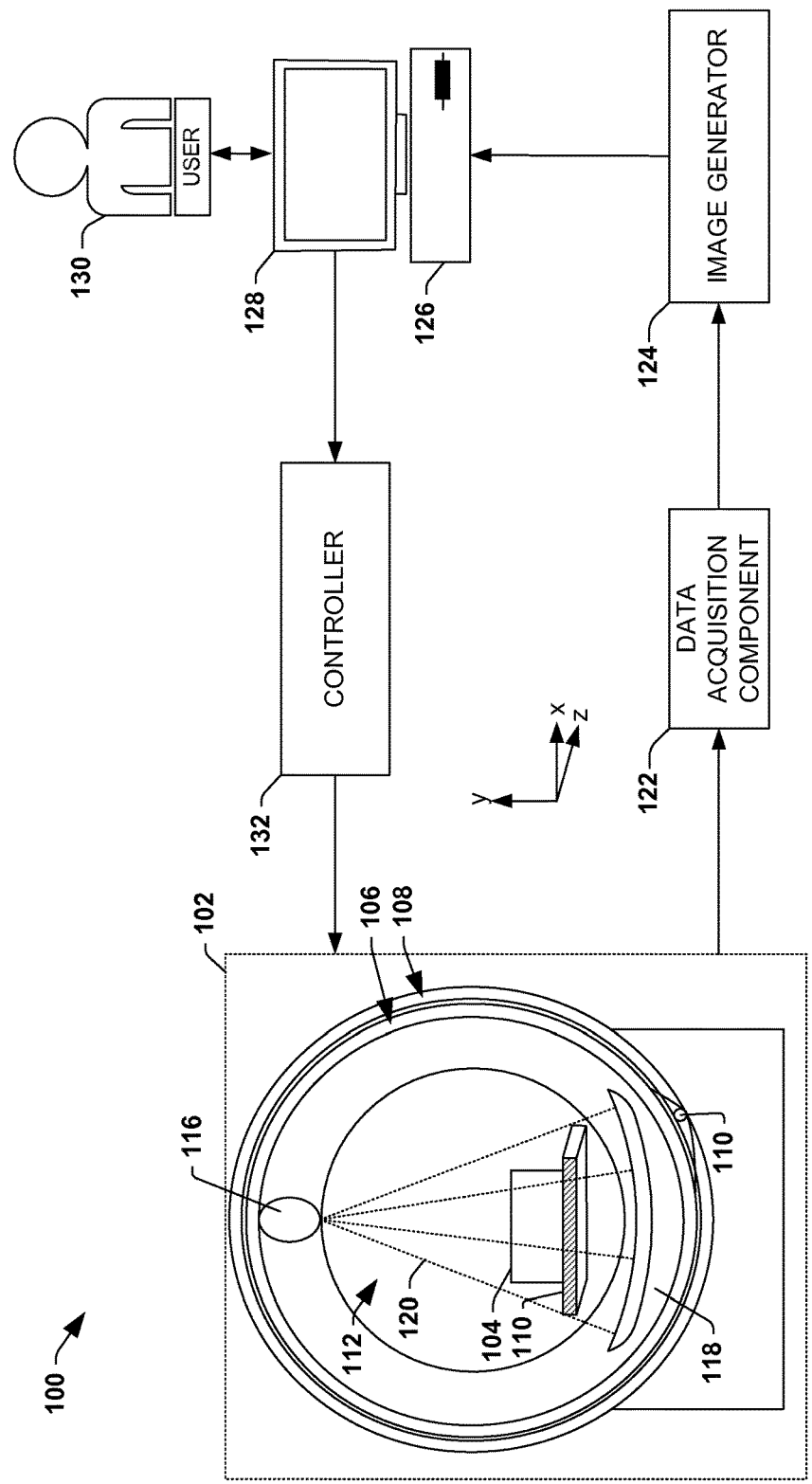
FIG. 1 is a schematic block diagram illustrating an example radiation system.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

According to some embodiments, a detector array is provided. The detector array comprises a first detector cell comprising a first scintillator. The first scintillator comprises a first detection surface through which a radiation photon impinging the first scintillator enters the first scintillator. The first detector cell includes a first solar cell that converts first light energy into first electrical energy. The detector array comprises a second detector cell comprising a second scintillator. The second scintillator comprises a second detection surface through which a radiation photon impinging the second scintillator enters the second scintillator. The second detector cell includes a second solar cell that converts second light energy into second electrical energy. In an example, the second detection surface is substantially parallel to the first detection surface and the second detection surface is not coplanar with the first detection surface. As such, an effective scintillator thickness, defined as a distance that the radiation photon travels through the first scintillator or the second scintillator, can be longer than the scintillator thickness.

FIG. 1 illustrates a radiation system 100 where the techniques and/or systems described herein may be employed. In the illustrated embodiment, the radiation system 100 is a computed tomography (CT) system, although the systems and/or techniques described herein may find applicability to other radiation imaging systems such as line-scan systems, mammography systems, and/or diffraction systems, for example. The radiation system 100 thus merely provides an example arrangement and is not intended to be interpreted in a limiting manner, such as necessarily specifying the location, inclusion, and/or relative position of the components depicted therein. By way of example, in some embodiments, a data acquisition component 122 is part of a detector array 118 and/or is located on a rotating gantry 106 of an examination unit 102.

In the example radiation system 100, the examination unit 102 is configured to examine objects 104 (e.g., suitcases, cargo, patients, etc.). The examination unit 102 comprises the rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). During an examination of an object 104, the object 104 is placed on a support article 110, such as a bed or conveyor belt, for example, and positioned within an examination region 112 (e.g., a hollow bore in the rotating gantry 106), where the object 104 is exposed to radiation 120.

The rotating gantry 106 may surround a portion of the examination region 112 and may comprise a radiation source 116 (e.g., an ionizing radiation source such as an x-ray source and/or gamma-ray source) and the detector array 118. The detector array 118 is typically mounted on a substantially diametrically opposite side of the rotating gantry 106 relative to the radiation source 116, and during an examination of the object 104, the rotating gantry 106 (e.g., including the radiation source 116 and detector array 118) is rotated about the object 104. Typically, a plane in which the rotating gantry 106 is rotated is defined as an x,y plane and a direction in which the object is translated into and out of the examination region 112 is referred to as the z-direction. Because the radiation source 116 and the detector array 118 are mounted to a same rotating gantry 106, a relative position between the detector array 118 and the radiation source 116 is substantially maintained during the rotation of the rotating gantry 106.

During the examination of the object 104, the radiation source 116 emits cone-beam and/or fan-beam radiation configurations from a focal spot of the radiation source 116 (e.g., a region within the radiation source 116 from which radiation 120 emanates) into the examination region 112. Such radiation 120 may be emitted substantially continuously and/or may be emitted intermittently (e.g., a brief pulse of radiation 120 is emitted followed by a resting period during which the radiation source 116 is not activated). Further, the radiation 120 may be emitted at a single energy spectrum or multiple energy spectrums depending upon, among other things, whether the radiation system 100 is configured as a single-energy system or a multi-energy (e.g., dual-energy) system.

As the emitted radiation 120 traverses the object 104, the radiation 120 may be attenuated differently by different aspects of the object 104. Because different aspects attenuate different percentages of the radiation 120, the number of photons and/or energy levels of respective photons detected by detector cells of the detector array 118 may vary. For example, more dense aspects of the object(s) 104, such as a bone, may attenuate more of the radiation 120 (e.g., causing fewer photons to impinge upon a region of the detector array 118 shadowed by the more dense aspects) than less dense aspects, such as tissue.

The detector array 118 comprises a plurality of detector cells respectively configured to convert radiation photons impinging the detector cell into electrical charge to produce analog signals. In some embodiments, the detector array 118 is a one-dimensional array, where the detector array 118 comprises a plurality of columns of detector cells (e.g., extending in the x,y plane) and a single row of detector cells (e.g., extending in the z-direction, which goes into the page in FIG. 1). In other embodiments, the detector array 118 is a two-dimensional array, where the detector array 118 comprises a plurality of columns of detector cells and a plurality of rows of detector cells.

The detector cells respectively comprise a scintillator configured to generate light energy (e.g., luminescent photons within a visible light wavelength spectrum) responsive to a radiation photon interacting with the scintillator. A solar cell can convert the light energy into electrical energy based upon light detected by the solar cell.

The analog signals that are generated by respective detector cells of the detector array 118 can be transmitted from the detector array 118 to the data acquisition component 122 operably coupled to the detector array 118. The analog signal(s) may carry information indicative of the radiation detected by the detector array 118 (e.g., such as an amount of charge measured over a sampling period and/or an energy level of detected radiation).

The data acquisition component 122 is configured to convert the analog signals output by the detector array 118 into digital signals and/or to compile signals that were transmitted within a predetermined time interval, or measurement interval, using various techniques (e.g., integration, photon counting, etc.). The compiled signals are typically in projection space and are, at times, referred to as projections. A projection may be representative of the information collected or measurements acquired by respective detector cells of the detector array 118 during an interval of time or a view, where a view corresponds to data collected while the radiation source 116 was at a particular view-angle or within a particular angular range relative to the object 104.

Data (e.g., the digital signals and/or the projections) generated by the data acquisition component 122 may be transmitted to an image generation component 124 operably coupled to the data acquisition component 122. The image generation component 124 is configured to convert at least some of the data from projection space to image space using suitable analytical, iterative, and/or other reconstruction techniques (e.g., tomosynthesis reconstruction, back-projection, iterative reconstruction, etc.). The images generated by the image generation component 124 may be in two-dimensional space and/or three-dimensional space and may be representative of the degree of attenuation through various aspects of the object 104 for a given view, may be representative of the density of various aspects of the object 104, and/or may be representative of the z-effective of various aspects of the object 104, for example.

The example radiation system 100 further comprises a terminal 126, or workstation (e.g., a computer), that may be configured to receive images output by the image generation component 124, which may be displayed on a monitor 128 to a user 130 (e.g., security personnel, medical personnel, etc.). In this way, the user 130 can inspect the image(s) to identify areas of interest within the object 104, for example. The terminal 126 can also be configured to receive user input which can direct operations of the examination unit 102 (e.g., a speed to rotate, a speed and direction of the support article 110, etc.), for example.

In the example radiation system 100, a controller 132 is operably coupled to the terminal 126. The controller 132 may be configured to control operations of the examination unit 102, for example. By way of example, in one embodiment, the controller 132 may be configured to receive information from the terminal 126 and to issue instructions to the examination unit 102 indicative of the received information (e.g., change the position of the support article relative to the radiation source 116, etc.).

Figure 2A:
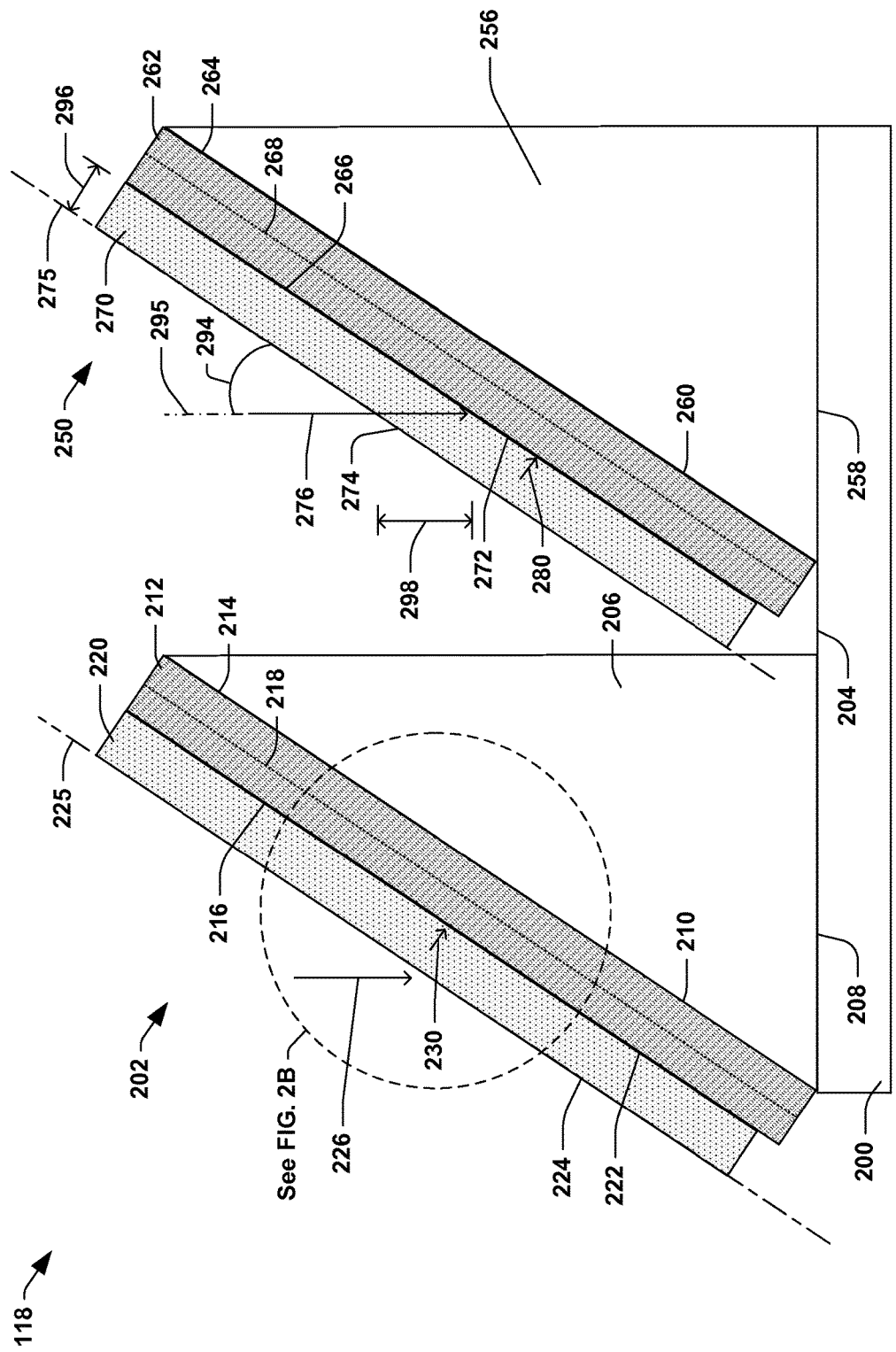
FIG. 2A is a cross-sectional view of an example detector array.

FIG. 2A illustrates a cross-sectional view of a portion of an example indirect conversion detector array 118. The detector array 118 can include one or more circuit components 200. The circuit component(s) 200 include any number of structures, components, parts, etc., including, but not limited to, printed circuit boards (PCB) or other components that can support and electrically connect electronic components. In this example, the detector array 118 is illustrated as including a single circuit component 200, though, in other examples, may include a plurality of circuit components 200.

The circuit component 200 can include a first detector cell 202 supported on a first surface 204 of the circuit component 200. According to some examples, the first detector cell 202 is electrically connected to the circuit component 200. The first detector cell 202 can include a first support structure 206 that is supported on the first surface 204. In the illustrated example, the first support structure 206 has a generally triangular shape (e.g., right triangle). The first support structure 206 includes a first base surface 208 and a first support surface 210. The first base surface 208 can be attached to, supported by, etc. the first surface 204 of the circuit component 200. The first support surface 210, which may define the hypotenuse of the first support structure 206, can face in a direction away from the first surface 204 of the circuit component 200. The first support structure 206 includes any number of materials that have at least some degree of rigidity/inflexibility so as to support structures, components, etc. thereupon. For example, the first support structure 206 may include a ceramic material, composite materials, plastics, etc.

The first detector cell 202 can include a first solar cell 212. The first solar cell 212 can include a solar base surface 214 and a solar attachment surface 216. The solar attachment surface 216 can face in a direction towards the first surface 204 of the circuit component 200. In this example, the solar attachment surface 216 can be attached to and/or supported by the first support surface 210 of the first support structure 206. The first solar cell 212 can be attached in any number of ways to the first support structure 206, such as with adhesives, mechanical fasteners, locking structures, or the like. The solar attachment surface 216 can face in a direction away from the first surface 204 of the circuit component 200.

The first solar cell 212 is an electrical device that can convert light energy into electricity, such as by the photovoltaic effect. The first solar cell 212 includes any number of different types of solar cells, including photovoltaic cells, photoelectric cells, or the like. In general, the first solar cell 212 has a p-n junction 218, which is a boundary/interface between two types of semiconductor materials (e.g., p-type and n-type materials). In an example, the first solar cell 212 can operate with a non-reverse bias, such as with a zero bias, for example.

The first detector cell 202 can include a first scintillator 220. The first scintillator 220 comprises a first light emission surface 222 and a first detection surface 224. The first light emission surface 222 can face in a direction towards the first solar cell 212 and the first support structure 206. The first light emission surface 222 can be attached to, supported by, etc. the solar attachment surface 216 of the first solar cell 212.

The first solar cell 212 is positioned proximate the first light emission surface 222 of the first scintillator 220. By being proximate, the first scintillator 220 and the first solar cell 212 can be in contact (as illustrated) or, in other examples, the first scintillator 220 and the first solar cell 212 may be spaced a distance apart from the first scintillator 220 such that the first light emission surface 222 and the solar attachment surface 216 are not in contact.

In an example, the first detection surface 224 defines a generally planar surface and extends along a first detection surface plane 225. According to some examples, the first surface 204 of the circuit component 200 faces the first scintillator 220. In an example, the first surface 204 of the circuit component 200 is not parallel to the first detection surface 224 of the first scintillator 220.

The first scintillator 220 includes any number of materials. For example, the first scintillator 220 can include a crystalline material (e.g., Cadmium Tungstate (CWO), Zinc Tungstate, etc.), a ceramic material (e.g., Gadolinium Oxysulfide (GOS)), and/or other scintillating material(s) known to those skilled in the art. In this example, the first scintillator 220 may include an optically translucent material to reduce lateral scattering of radiation photons 226. According to some examples, the first scintillator 220 can convert the radiation photon(s) 226 that impinges the first scintillator 220 into first light energy 230. In some examples, this first light energy 230 includes luminescent photons in the visible spectral range, from about 400 nm to about 600 nm. However, it will be appreciated that the scope of the instant disclosure and/or the claimed subject matter is not intended to be limited to such a range.

In operation, the first scintillator 220 includes the first detection surface 224 through which the radiation photon 226 impinging the first scintillator 220 enters the first scintillator 220. With the radiation photon 226 entering the first scintillator 220, the first scintillator 220 can convert the radiation photon 226 into the first light energy 230. In some examples, the first scintillator 220 can include a reflective material (e.g., around a perimeter of the first scintillator 220) that can reflect the first light energy 230 back into the first scintillator 220. As such, most, if not all, of the first light energy 230 can remain trapped within the first detector cell 202 and may be detected by the first solar cell 212. The first solar cell 212 can then convert the first light energy 230 into first electrical energy.

The circuit component 200 can include a second detector cell 250 supported on the first surface 204 of the circuit component 200. According to some examples, the second detector cell 250 is electrically connected to the circuit component 200. The second detector cell 250 can be generally identical to the first detector cell 202. For example, the second detector cell 250 can include a second support structure 256 that is supported on the first surface 204. In the illustrated example, the second support structure 256 has a generally triangular shape (e.g., right triangle). The second support structure 256 includes a second base surface 258 and a second support surface 260. The second base surface 258 can be attached to, supported by, etc. the first surface 204 of the circuit component 200. The second support surface 260, which may define the hypotenuse of the second support structure 256, can face in a direction away from the first surface 204 of the circuit component 200. The second support structure 256 includes any number of materials that have at least some degree of rigidity/inflexibility so as to support structures, components, etc. thereupon. For example, the second support structure 256 may include a ceramic material, composite materials, plastics, etc.

The second detector cell 250 can include a second solar cell 262. The second solar cell 262 can include a solar base surface 264 and a solar attachment surface 266. The solar attachment surface 266 can face in a direction towards the first surface 204 of the circuit component 200. In this example, the solar attachment surface 266 can be attached to and/or supported by the second support surface 260 of the second support structure 256. The second solar cell 262 can be attached in any number of ways to the second support structure 256, such as with adhesives, mechanical fasteners, locking structures, or the like. The solar attachment surface 266 can face in a direction away from the first surface 204 of the circuit component 200.

The second solar cell 262 is an electrical device that can convert light energy into electricity, such as by the photovoltaic effect. The second solar cell 262 includes any number of different types of solar cells, including photovoltaic cells, photoelectric cells, or the like. In general, the second solar cell 262 has a p-n junction 268, which is a boundary/interface between two types of semiconductor materials (e.g., p-type and n-type materials). In an example, the second solar cell 262 can operate with a non-reverse bias, such as with a zero bias, for example.

The second detector cell 250 can include a second scintillator 270. The second scintillator 270 comprises a second light emission surface 272 and a second detection surface 274. The second light emission surface 272 can face in a direction towards the second solar cell 262 and the second support structure 256. The second light emission surface 272 can be attached to, supported by, etc. the solar attachment surface 266 of the second solar cell 262.

The second solar cell 262 is positioned proximate the second light emission surface 272 of the second scintillator 270. By being proximate, the second scintillator 270 and the second solar cell 262 can be in contact (as illustrated) or, in other examples, the second scintillator 270 and the second solar cell 262 may be spaced a distance apart from the second scintillator 270 such that the second light emission surface 272 and the solar attachment surface 266 are not in contact.

In an example, the second detection surface 274 defines a generally planar surface and extends along a second detection surface plane 275. According to some examples, the second surface 254 of the circuit component 200 faces the second scintillator 270. The first surface 204 of the circuit component 200 is not parallel to the second detection surface 274 of the second scintillator 270. In this example, the second detection surface 274 may be substantially parallel to the first detection surface 224. The second detection surface 274 may not be coplanar with the first detection surface 224. Rather, the first detection surface 224 extends along a plane (e.g., the first detection surface plane 225) that is parallel to but not coplanar with a plane (e.g., the second detection surface plane 275) along which the second detection surface 274 extends.

The second scintillator 270 includes any number of materials. For example, the second scintillator 270 can include a crystalline material (e.g., Cadmium Tungstate (CWO), Zinc Tungstate, etc.), a ceramic material (e.g., Gadolinium Oxysulfide (GOS)), and/or other scintillating material(s) known to those skilled in the art. In this example, the second scintillator 270 may include an optically translucent material to reduce lateral scattering of radiation photons 276. According to some examples, the second scintillator 270 can convert the radiation photon(s) 276 that impinges the second scintillator 270 into second light energy 280. In some examples, this second light energy 280 includes luminescent photons in the visible spectral range, from about 400 nm to about 600 nm. However, it will be appreciated that the scope of the instant disclosure and/or the claimed subject matter is not intended to be limited to such a range.

In operation, the second scintillator 270 includes the second detection surface 274 through which the radiation photon 276 impinging the second scintillator 270 enters the second scintillator 270. With the radiation photon 276 entering the second scintillator 270, the second scintillator 270 can convert the radiation photon 276 into the second light energy 280. In some examples, the second scintillator 270 can include a reflective material (e.g., around a perimeter of the second scintillator 270) that can reflect the second light energy 280 back into the second scintillator 270. As such, most, if not all, of the second light energy 280 can remain trapped within the second detector cell 250 and may be detected by the second solar cell 262. The second solar cell 262 can then convert the second light energy 280 into second electrical energy.

While the example detector array 118 of FIG. 2A is illustrated as including two detectors cells (e.g., the first detector cell 202 and the second detector cell 250), the detector array 118 is not so limited. Rather, the detector array 118 can include any number of detector cells (e.g., one or more) that may be arranged in rows and/or columns.

Figure 2B:
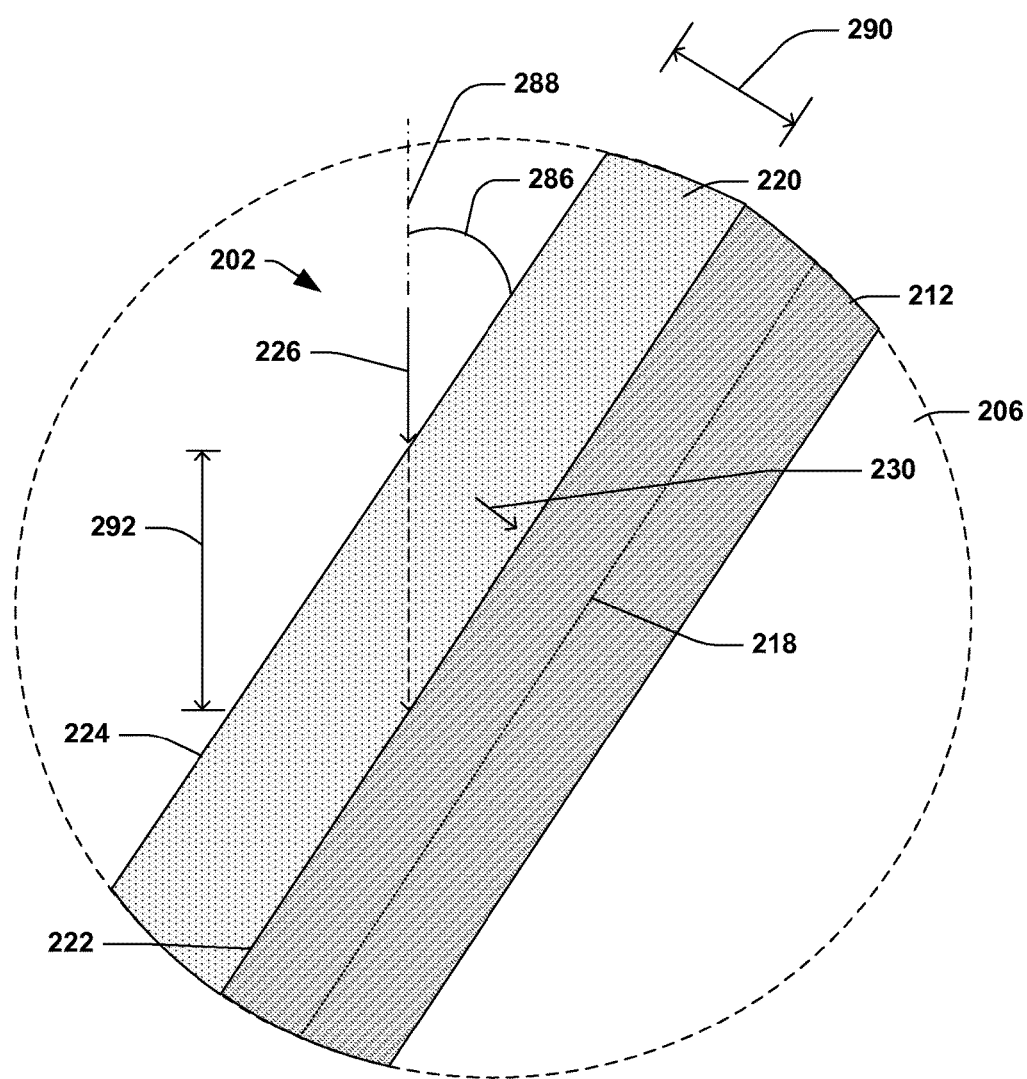
FIG. 2B is a cross-sectional view of an example detector array.

Turning to FIG. 2B, a portion of the first detector cell 202 is illustrated. In this example, the first detection surface 224, which extends along the first detection surface plane 225, can form a first incidence angle 286 with respect to a first radiation photon axis 288 along which the radiation photon 226 impinging the first scintillator 220 travels. In some examples, the first incidence angle 286 is greater than 0 degrees and less than 90 degrees. In another example, the first incidence angle 286 is between about 5 degrees to about 25 degrees. In an example, the first incidence angle 286 is about 14 degrees.

The first scintillator 220 has a scintillator thickness 290. The scintillator thickness 290 can be between about 0.1 mm to about 0.9 mm. In an example, the scintillator thickness 290 is about 0.5 mm. The first scintillator 220 can be applied in any number of ways to the first solar cell 212, such as by spraying, deposition, or the like. In some embodiments, the radiation photon 226 impinges the first scintillator 220 at the first incidence angle 286. An effective scintillator thickness 292 can be defined as a distance that the radiation photon 226 travels through the first scintillator 220 before impinging the first solar cell 212. In this example, the first scintillator 220 can have a longer effective scintillator thickness 292 than the scintillator thickness 290. For example, the effective scintillator thickness 292 can be at least 1 mm.

Referring now to the second detector cell 250 in FIG. 2A, the second detection surface 274, which extends along the second detection surface plane 275, can form a second incidence angle 294 with respect to a second radiation photon axis 295 along which the radiation photon 276 impinging the second scintillator 270 travels. In some examples, the second incidence angle 294 is greater than 0 degrees and less than 90 degrees. In another example, the second incidence angle 294 is between about 5 degrees to about 25 degrees. In an example, the second incidence angle 294 is about 14 degrees.

The second scintillator 270 has a scintillator thickness 296. The scintillator thickness 296 can be between about 0.1 mm to about 0.9 mm. In an example, the scintillator thickness 296 is about 0.5 mm. The second scintillator 270 can be applied in any number of ways to the second solar cell 262, such as by spraying, deposition, or the like. In some embodiments, the radiation photon 276 impinges the second scintillator 270 at the second incidence angle 294. An effective scintillator thickness 298 can be defined as a distance that the radiation photon 226 travels through the second scintillator 270 before impinging the second solar cell 262. In this example, the second scintillator 270 can have a longer effective scintillator thickness 298 than the scintillator thickness 296. For example, the effective scintillator thickness 298 can be at least 1 mm.

Figure 3:
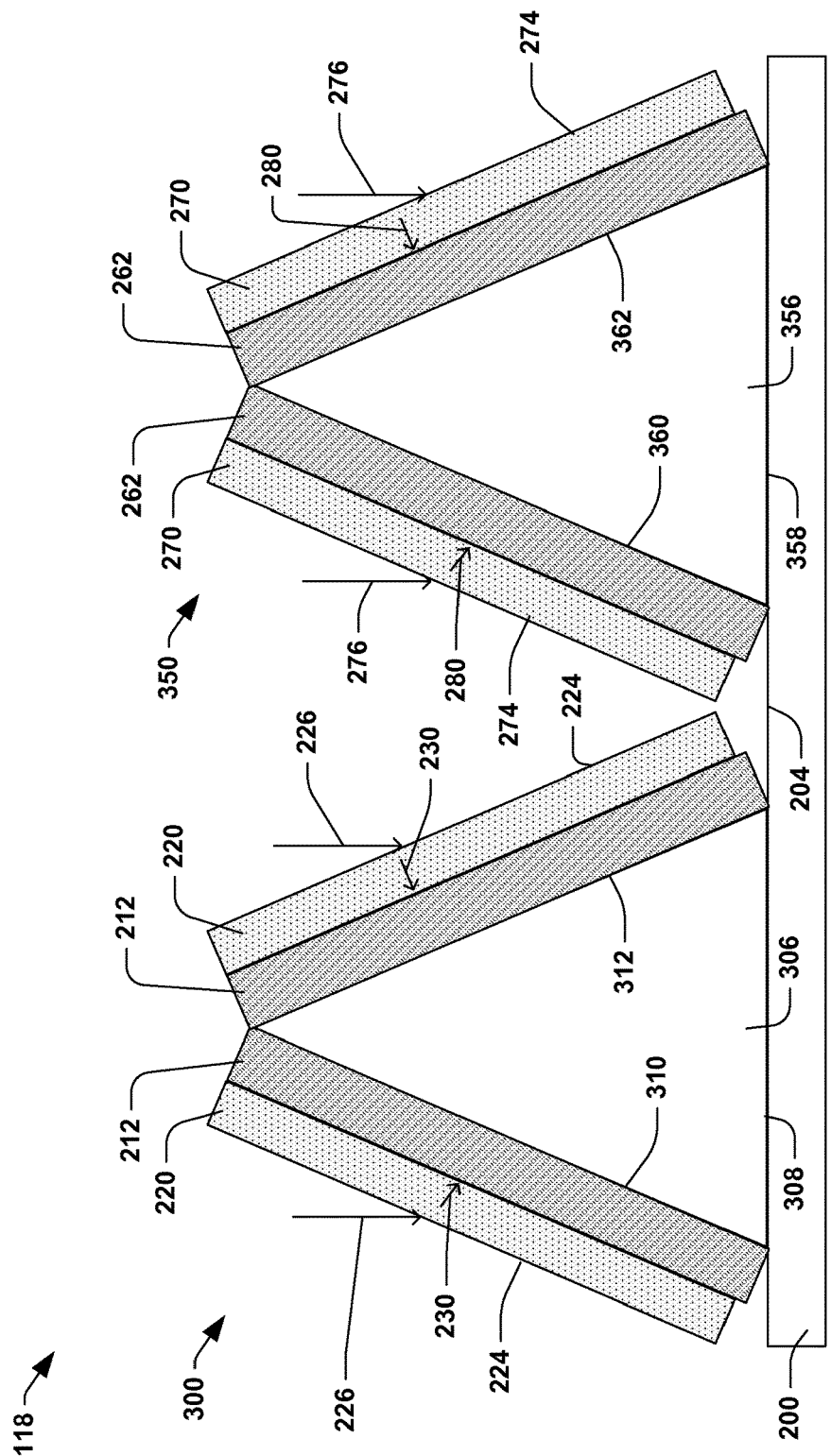
FIG. 3 is a perspective view of an example detector array.

Turning to FIG. 3, a second example of the detector array 118 is illustrated. In this example, the detector array 118 can include a first detector cell 300. The first detector cell 300 can include a first support structure 306 that is supported on the first surface 204 of the circuit component 200. In the illustrated example, the first support structure 306 has a generally triangular shape. While any number of shapes are envisioned, in this example, the triangular shape of the first support structure 306 includes an isosceles triangle having two equal sides. The first support structure 306 is not so limited, and, in other examples, may include an equilateral triangle, or the like.

The first support structure 306 can include a first base surface 308. The first base surface 308 can be attached to, supported by, etc., the first surface 204 of the circuit component 200. The first support structure 306 can include a first support surface 310 and a second support surface 312. The first support surface 310 and the second support surface 312 can face in a direction away from the first surface 204 of the circuit component 200. In this example, the first support surface 310 and the second support surface 312 can have generally identical lengths, and may form generally identical angles with respect to the first base surface 308. The first support structure 306 includes any number of materials that have at least some degree of rigidity/inflexibility so as to support structures, components, etc. thereupon. For example, the first support structure 306 may include a ceramic material, composite materials, plastics, etc.

The first detector cell 300 can include a plurality of first solar cells 212. In this example, the first solar cells 212 can be attached to and/or supported by the first support surface 310 and the second support surface 312. As such, the first solar cells 212 can face in generally opposite directions. The first detector cell 300 can include a plurality of first scintillators 220 that are attached to the first solar cells 212. In an embodiment, the detection surfaces (e.g., the first detection surfaces 224) of the first solar cells 212 are mirror images relative to each other. That is, the detection surfaces (e.g., the first detection surfaces 224) of the first solar cells 212 can be axially symmetric with respect to each other.

The detector array 118 can include a second detector cell 350. The second detector cell 350 can include a second support structure 356 that is supported on the first surface 204 of the circuit component 200. In the illustrated example, the second support structure 356 has a generally triangular shape. While any number of shapes are envisioned, in this example, the triangular shape of the second support structure 356 includes an isosceles triangle having two equal sides. The second support structure 356 is not so limited, and, in other examples, may include an equilateral triangle, or the like.

The second support structure 356 can include a second base surface 358. The second base surface 358 can be attached to, supported by, etc., the first surface 204 of the circuit component 200. The second support structure 356 can include a third support surface 360 and a fourth support surface 362. The third support surface 360 and the fourth support surface 362 can face in a direction away from the first surface 204 of the circuit component 200. In this example, the third support surface 360 and the fourth support surface 362 can have generally identical lengths, and may form generally identical angles with respect to the second base surface 358. The second support structure 356 includes any number of materials that have at least some degree of rigidity/inflexibility so as to support structures, components, etc. thereupon. For example, the second support structure 356 may include a ceramic material, composite materials, plastics, etc.

The second detector cell 350 can include a plurality of second solar cells 262. In this example, the second solar cells 262 can be attached to and/or supported by the third support surface 360 and the fourth support surface 362. As such, the second solar cells 262 can face in generally opposite directions. The second detector cell 350 can include a plurality of second scintillators 270 that are attached to the second solar cells 262. In an embodiment, the detection surfaces (e.g., the second detection surfaces 274) of the second solar cells 262 are mirror images relative to each other. That is, the detection surfaces (e.g., the second detection surfaces 274) of the second solar cells 262 can be axially symmetric with respect to each other.

Figure 4:
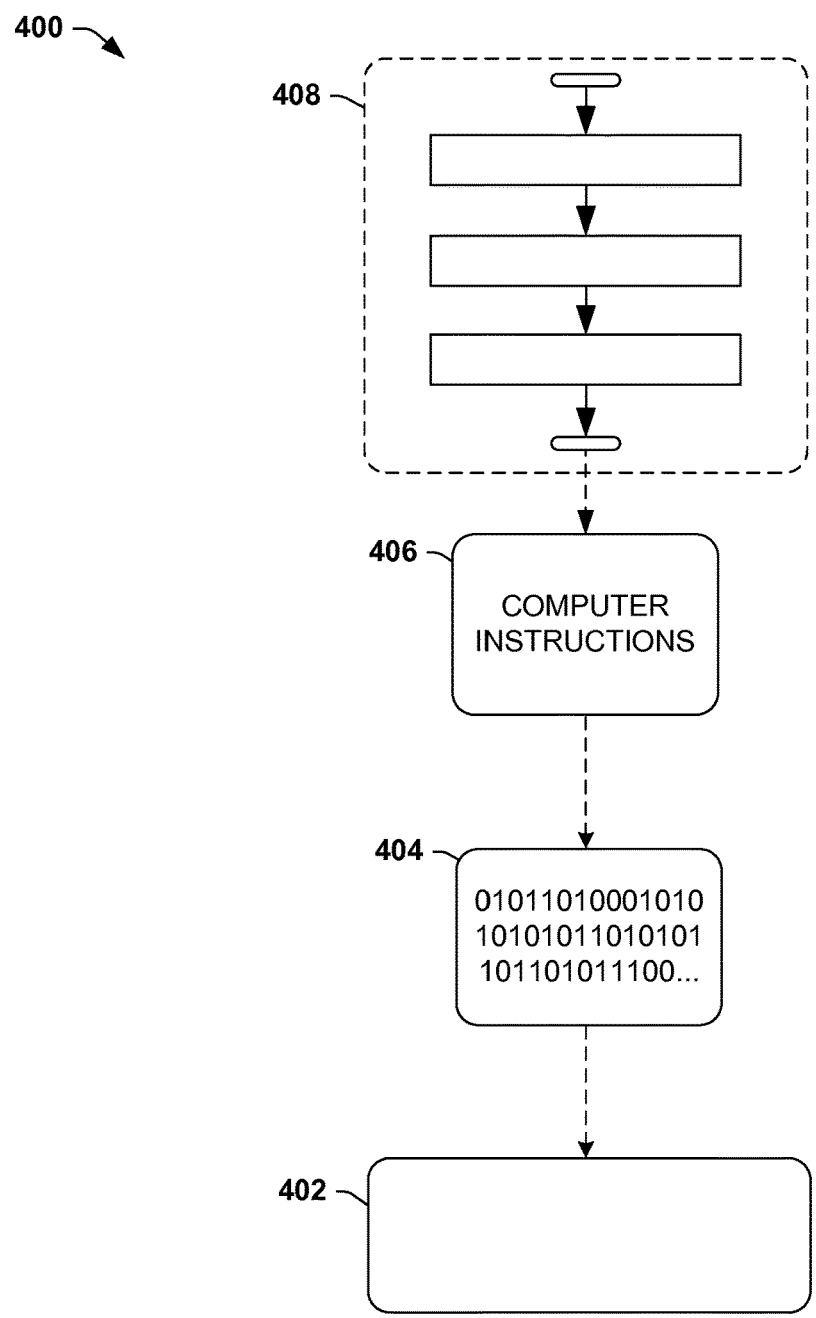
FIG. 4 is an illustration of an example computer-readable medium comprising processor-executable instructions configured to embody one or more of the provisions set forth herein.

Still another embodiment involves a computer-readable medium comprising processor-executable instructions configured to implement one or more of the techniques presented herein. An example computer-readable medium that may be devised in these ways is illustrated in FIG. 4, wherein the implementation 400 comprises a computer-readable medium 402 (e.g., a flash drive, CD-R, DVD-R, or a platter of a hard disk drive), on which is encoded computer-readable data 404. This computer-readable data 404 in turn comprises a set of processor-executable instructions 406 configured to operate according to one or more of the principles set forth herein. In one such embodiment of implementation 400, the processor-executable instructions 406 may be configured to perform a method 408 when the processor-executable instructions 406 are executed by a processing unit. In another such embodiment, the processor-executable instructions 406 may be configured to implement a system, such as at least some of the exemplary radiation system 100 of FIG. 1, for example. Many such computer-readable media may be devised by those of ordinary skill in the art that are configured to operate in accordance with one or more of the techniques presented herein.

Although the subject matter has been described in language specific to structural features or methodological acts, it is to be understood that the subject matter of the appended claims is not necessarily limited to the specific features or acts described above. Rather, the specific features and acts described above are disclosed as embodiment forms of implementing at least some of the claims.

Various operations of embodiments are provided herein. The order in which some or all of the operations are described should not be construed to imply that these operations are necessarily order dependent. Alternative ordering will be appreciated given the benefit of this description. Further, it will be understood that not all operations are necessarily present in each embodiment provided herein. Also, it will be understood that not all operations are necessary in some embodiments.

Moreover, "exemplary" is used herein to mean serving as an example, instance, illustration, etc., and not necessarily as advantageous. As used in this application, "or" is intended to mean an inclusive "or" rather than an exclusive "or." In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes," "having," "has," "with," or variants thereof are used, such terms are intended to be inclusive in a manner similar to the term "comprising." The claimed subject matter may be implemented as a method, apparatus, or article of manufacture (e.g., as software, firmware, hardware, or any combination thereof).

As used in this application, the terms "component," "module," "system," "interface," and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. For example, a first channel and a second channel generally corresponds to channel A and channel B or two different or two identical channels or the same channel.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure. In addition, while a particular feature of the disclosure may have been disclosed with respect to only one of several implementations, such feature may be combined with one or more other features of the other implementations as may be desired and advantageous for any given or particular application.

What is claimed is:

1. A detector array for a radiation system, the detector array comprising:
    a first detector cell comprising:
        a first scintillator configured to convert a first radiation photon impinging the first scintillator into first light energy; and
        a first solar cell configured to convert the first light energy into first electrical energy, the first solar cell including a solar base surface configured to receive the first light energy and a solar attachment surface opposite the solar base surface;
    a circuit component including a first surface substantially perpendicular to an expected direction of travel of the first radiation photon; and
    a first support structure configured to support the first detector cell on the first surface of the circuit component, the first support structure having a substantially triangular cross-sectional shape, the first support structure comprising:
        a first base surface, the first surface of the circuit component configured to mechanically support the first base surface of the first support structure; and
        a first support surface forming an acute angle with the first base surface of the first support structure, the first support surface configured to mechanically support the first solar cell.

2. The detector array of claim 1, comprising:
    a second detector cell comprising:
        a second scintillator configured to convert a second radiation photon impinging the second scintillator into second light energy, wherein:
            the first scintillator comprises a first detection surface through which the first radiation photon impinging the first scintillator enters the first scintillator; and
            the second scintillator comprises a second detection surface through which the second radiation photon impinging the second scintillator enters the second scintillator, the second detection surface substantially parallel to the first detection surface and the second detection surface not coplanar with the first detection surface.

3. The detector array of claim 1, wherein the first surface of the circuit component is not parallel to a first detection surface, of the first scintillator, through which the radiation photon impinging the first scintillator enters the first scintillator.

4. The detector array of claim 1, comprising:
    a second detector cell comprising:
        a second scintillator configured to convert a second radiation photon impinging the second scintillator into second light energy, wherein:

the first scintillator comprises a first detection surface through which the first radiation photon impinging the first scintillator enters the first scintillator; and the second scintillator comprises a second detection surface through which the radiation photon impinging the second scintillator enters the second scintillator, the second detection surface a mirror image relative to the first detection surface.

5. The detector array of claim 1, wherein the first scintillator comprises a first detection surface through which the first radiation photon impinging the first scintillator enters the first scintillator and a first light emission surface through which the first light energy exits the first scintillator, the first detection surface extending along a first detection surface plane that forms a first incidence angle with respect to a first radiation photon axis along which the first radiation photon impinging the first scintillator is expected to travel, the first incidence angle greater than 0° and less than 90°.

6. The detector array of claim 5, wherein the first incidence angle is between about 5° to about 25°.

7. The detector array of claim 1, wherein the first solar cell has a p-n junction.

8. The detector array of claim 1, wherein the first solar cell is configured to operate with a non-reverse bias.

9. The detector array of claim 1, wherein the first scintillator has a scintillator thickness between about 0.1 mm to about 0.9 mm.

10. The detector array of claim 9, wherein the first scintillator has an effective scintillator thickness of at least 1 mm.

11. The detector array of claim 1, wherein the first scintillator has a scintillator thickness that is less than an effective scintillator thickness of the first scintillator.

12. A detector array for a radiation system, the detector array comprising:
- a first detector cell comprising:
  - a first scintillator configured to convert a first radiation photon impinging the first scintillator into first light energy, the first scintillator comprising a first detection surface through which the first radiation photon impinging the first scintillator enters the first scintillator; and
  - a first solar cell configured to convert the first light energy into first electrical energy, the first solar cell including a solar base surface configured to receive the first light energy and a solar attachment surface opposite the solar base surface;
- a second detector cell comprising:
  - a second scintillator configured to convert a second radiation photon impinging the second scintillator into second light energy, the second scintillator comprising a second detection surface through which the second radiation photon impinging the second scintillator enters the second scintillator;
  - wherein the second detection surface is substantially parallel to the first detection surface and the second detection surface is not coplanar with the first detection surface;
- a circuit component including a first surface substantially perpendicular to an expected direction of travel of the first radiation photon; and
- a first support structure configured to support the first detector cell on the first surface of the circuit component, the first support structure having a substantially triangular cross-sectional shape, the first support structure comprising:
  - a first base surface, the first surface of the circuit component configured to mechanically support the first base surface of the first support structure; and
  - a first support surface forming an acute angle with the first base surface of the first support structure, the first support surface configured to mechanically support the first solar cell.

13. The detector array of claim 12, further comprising a second support structure configured to support the second detector cell on the first surface of the circuit component, the second support structure having a substantially triangular cross-sectional shape.

14. The detector array of claim 12, wherein the first detection surface extends along a first detection surface plane that forms a first incidence angle with respect to a first radiation photon axis along which the first radiation photon impinging the first scintillator is expected to travel, the first incidence angle greater than 0° and less than 90°.

15. The detector array of claim 14, wherein the first incidence angle is between about 5° and about 25°.

16. The detector array of claim 12, wherein the first scintillator has a scintillator thickness between about 0.1 mm to about 0.9 mm.

17. The detector array of claim 12, wherein the first scintillator has an effective scintillator thickness of at least 1 mm.

18. A radiation system comprising:
- a radiation source configured to emit a radiation photon;
- a first detector cell comprising:
  - a first scintillator configured to convert the radiation photon impinging the first scintillator into first light energy, the first scintillator comprising a first detection surface through which the radiation photon impinging the first scintillator enters the first scintillator and a first light emission surface through which the first light energy exits the first scintillator, the first detection surface extending along a first detection surface plane that forms a first incidence angle with respect to a first radiation photon axis along which the radiation photon impinging the first scintillator travels, the first incidence angle greater than 0° and less than 90°;
- a circuit component including a first surface substantially perpendicular to an expected direction of travel of the radiation photon; and
- a first support structure configured to support the first detector cell on the first surface of the circuit component, the first support structure having a substantially triangular cross-sectional shape, the first support structure comprising:
  - a first base surface, the first surface of the circuit component configured to mechanically support the first base surface of the first support structure; and
  - a first support surface forming an acute angle with the first base surface of the first support structure, the first support surface configured to mechanically support the first detector cell.

19. The radiation system of claim 18, wherein the first incidence angle is between about 5° to about 25°.

20. The radiation system of claim 18, wherein the first scintillator has a scintillator thickness between about 0.1 mm to about 0.9 mm.

* * * * *